(12) United States Patent
Borsotti et al.

(10) Patent No.: US 6,297,391 B1
(45) Date of Patent: Oct. 2, 2001

(54) PROCESS FOR THE SYNTHESIS OF DIRICINOLEYPHOSPHATIDYLCHOLINE

(75) Inventors: Giampietro Borsotti, Novara; Ezio Battistel, Cameriano; Francesco Cellini; Rina Iannacone, both of Matera, all of (IT)

(73) Assignee: Metapontum Agrobios S.c.r.l., Metaponto (IT)

( * ) Notice: Subject to any disclaimer, the term of this patent is extended or adjusted under 35 U.S.C. 154(b) by 0 days.

(21) Appl. No.: 09/366,744

(22) Filed: Aug. 4, 1999

(30) Foreign Application Priority Data

Aug. 5, 1998 (IT) ............................................. MI98A1846

(51) Int. Cl.$^7$ .............................. C07C 53/00; C07F 9/02; C08H 3/00; C11D 1/28
(52) U.S. Cl. .................................. 554/82; 554/83; 554/80
(58) Field of Search .................... 554/82, 80, 83

(56) References Cited

FOREIGN PATENT DOCUMENTS 0 514 694 A1 * 11/1992 (EP) ............................. C12P/17/14

OTHER PUBLICATIONS

Greene, Protective Groups in Organic Synthesis, p. 10–13, 159, John Wiley and sons, 1985.*
Properties of unusual phospholipids. III: Synthesis, monolayer investigations and DSC studies of hydroxy octadeca(e)noic acids and diacylglycerophosphocholines derived therefrom, Chemistry and Physics of Lipids 90 (1997) 117–134.*
Properties of unusual phospholipids. III: Synthesis, CAPLUS registry file AN 1997:758864 rn 204009–48–3P.*
Paulus et al, Gas–liquid chromatographic determination of castor oil as methyl ricinoleate in lipstick, AN 1972:452220.*
Riebel, Preparation of N–phosphonomethyl glycine esters, Abstract and citation, AN 1997:187034.*
Lars Negelmann, et al., "Properties of Unusual Phospholipids. III: Synthesis, Monolayer Investigations and DSC Studies of Hydroxy Octadeca(e)noic Acids and Diacylglycerophosphocholines Derived Therefrom", Chemistry and Physics of Lipids, vol. 90, 1997, pp. 117–134.

* cited by examiner

Primary Examiner—Johann Richter
Assistant Examiner—Diedra Faulkner
(74) Attorney, Agent, or Firm—Oblon, Spivak, McClelland, Maier & Neustadt, P.C.

(57) ABSTRACT

Diricinoleylphosphatidylcholine (I) in an optically active form is obtained with good yields and a high purity by means of a process which comprises:
a) esterifying the terminal carboxylic group of ricinoleic acid (III) with an alcohol having from 1 to 4 carbon atoms to give the corresponding ester having formula (IV);
b) protecting the hydroxylic group of the ester of ricinoleic acid (IV) with a protecting group removable under bland operating conditions and isolating the ester of ricinoleic acid of which the hydroxylic group (V) is protected;
c) hydrolyzing the ester of ricinoleic acid of which the hydroxylic group (V) is protected and isolating the ricinoleic acid of which the hydroxylic group (VI) is protected;
d) acylating L-α-glycerophosphatidylcholine (II) with an imidazolic or triazolic derivative of the compound having formula (VI) and isolating the diricinoleylphosphatidylcholine of which the hydroxylic group (VII) is protected;
e) removing the protecting group from the hydroxylic group of the compound having formula (VII); and finally
f) recovering and purifying the compound having formula (I) by means of chromatography.

11 Claims, 1 Drawing Sheet

⇓ esterification

⇓ protection (protective R group)

⇓ ester hydrolysis acylation GPC

⇓

⇓ deprotection

PROCESS FOR THE SYNTHESIS OF DIRICINOLEYPHOSPHATIDYLCHOLINE

The present invention relates to a process for the synthesis of diricinoleylphosphatidylcholine (I) with good yields and a high purity.

The compound having formula (I) has been identified in ricinus seeds as an essential intermediate in the synthesis of triglycerides (M. Frentzen, "Acyl-transferases and Triacylglycerols" in "Lipid metabolism in plants", T. S. Moore, ed. CRC Press, New York, 1993, VI, pages 195–299).

The compound having formula (I) can be used in the detergent and cosmetic industries as an integrator or emulsifying agent or as a component in pharmaceutical and food formulations. The preparation of phosphatidylcholine by the direct synthesis of glycerophosphatidylcholine with a fatty acid (JP0499783), is known in the art. Operating according to this method, however, when ricinoleic acid is used, compound (I) is not obtained but only its condensation products.

Figure 1:
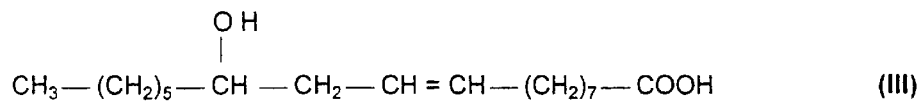
Figure 1:
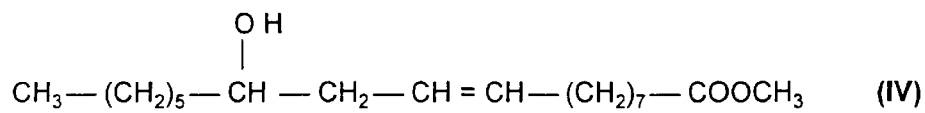
Figure 1:
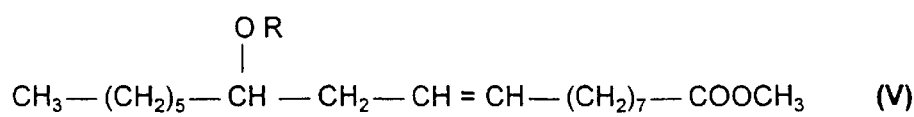
Figure 1:
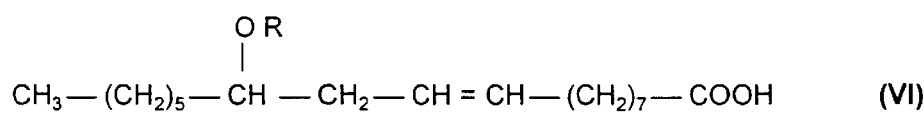
Figure 1:
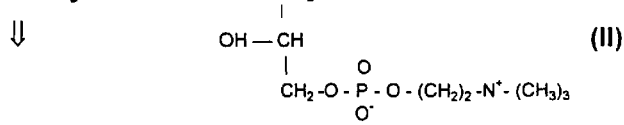
Figure 1:
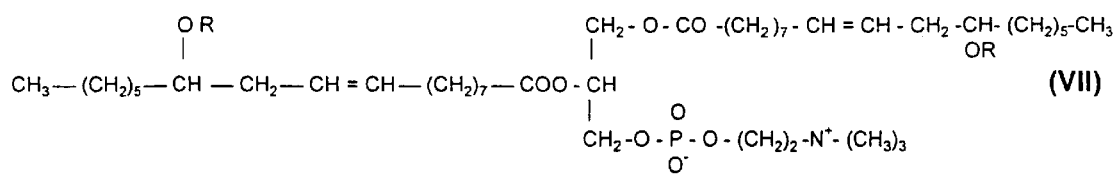
Figure 1:
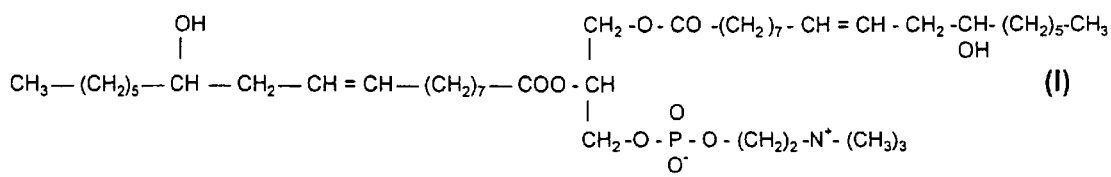

It has now been found that it is possible to obtain diricinoleylphosphatidylcholine (I) with good yields and a high purity by means of a simple and economically convenient synthesis process illustrated in FIG. 1.

In accordance with this, the present invention relates to a process for the synthesis of diricinoleylphosphatidylcholine having formula (I) which comprises:

a) esterifying the terminal carboxylic group of ricinoleic acid (III) with an alcohol having from 1 to 4 carbon atoms to give the corresponding ester having formula (IV);

b) protecting the hydroxylic group of the ester of ricinoleic acid (IV) with a protecting group removable under bland operating conditions and isolating the ester of ricinoleic acid of which the hydroxylic group (V) is protected;

c) hydrolyzing the ester of ricinoleic acid of which the hydroxylic group (V) is protected and isolating the ricinoleic acid of the hydroxylic group (VI) is protected;

d) acylating L-α-glycerophosphatidylcholine (II) with an imidazolic or triazolic derivative of the compound having formula (VI) and isolating the diricinoleylphosphatidylcholine of which the hydroxylic group (VII) is protected;

e) removing the protecting group from the hydroxylic group of the compound having formula (VII); and finally f) recovering and purifying the compound having formula (I) by means of chromatography.

Step a)

In step (a) of the process of the present invention ricinoleic acid having formula (III) can be prepared by means of the saponification of castor oil using, for example, the method described by A. H. Blatt in "Organic Synthesis", Vol. II, page 53, ed. J. Wiley pub., New York, 1959. The product thus obtained, which has a titre of less than 90% and a dark yellow colour, is purified by means of fractionated crystallization or, preferably, by means of extraction with an organic solvent selected from tetrahydrofuran, dioxane, dimethoxyethane or ethers, such as for example diethyl ether, diisopropyl ether or dibutylether.

Diethyl ether and tetrahydrofuran (THF) are preferably used. In particular the latter method allows ricinoleic acid (III) with a purity higher than 99%, to be obtained.

Step b)

In step (b) of the process of the present invention, the rinicoleic acid (III) is esterified by reaction with an alcohol having from 1 to 4 carbon atoms to form the ester of this compound at the carboxylic end group (IV). Methyl alcohol is particularly preferred among the various alcohols.

The reaction is carried out by putting compound (III) and the alcohol in contact in a molar ratio ranging from 1:10 to 1:50, preferably from 1:20 to 1:40, in the presence of gaseous hydrochloric acid, and operating at a temperature ranging from 0 to 50° C.

The reaction is preferably carried out at 0° C. for about 10 minutes and then at room temperature (20–25° C.) for about 30 minutes.

The ester of rininoleic acid is then recovered and purified according to the known methods.

Step c)

In step (c) of the process of the present invention the hydroxylic group of the ester of ricinoleic acid (IV) is protected by means of reaction with a protecting group selected from:

1) 2-methoxy-ethoxymethylchloride (MEMCl) $CH_3OCH_2CH_2OCH_2Cl$;
2) 2,2,2-trichloethloethylchloroformiate (TROC) $Cl—COO—CH_2CCl_3$
3) chloromethyl-methyl-ether $CH_3—O—CH_2Cl$
4) chloromethylmethylsulfide $CH_3—S—CH_2Cl$ Among these 2-methoxy-ethoxymethylchloride and trichloroethylchloroformiate are particularly preferred for the purposes of the present invention.

These two groups have characteristics of stability under the reaction conditions of the process and can be easily removed under bland hydrolysis conditions.

Step d)

In step (d) of the process of the present invention the ester of ricinoleic acid having formula (V) is hydrolyzed. In particular, when the protecting group is MEMCl, alkaline hydrolysis conditions are adopted.

When, on the other hand, the protecting group is TROC the hydrolysis is carried out in the presence of enzymes such as for example the lipase of Pseudomonas.

At the end of the hydrolysis, the compound having formula (VI) is separated and recovered.

Step e)

In step e) of the process of the present invention L-α-glycerophosphatidylcholine (GPC) (II) is acylated with an imidazolinic or triazolinic derivative of ricinoleic acid of which the hydroxyl group is protected (VI).

Compound (II) can be obtained by the hydrolysis of soya lecithin or it can be synthesized starting from isopropylideneglycerol as described, for example, in the patent EP-486.100.

The acylation reaction is carried out in a solvent selected from N,N'-dimethylformamide, dimethylsulfoxide, tetramethylurea, N-methylpyrolidone in the presence of an anhydrous alkaline carbonate.

N,N'-dimethylformamide (DMF) is preferably used as solvent.

Examples of alkaline carbonates are selected from sodium carbonate, potassium carbonate, cesium carbonate.

A quantity of carbonate which is such as to give a molar ratio ranging from 0.1 to 5 moles per mole of GPC, is generally used. The DMF is used in a quantity ranging from 1000 to 2000 ml per mole of GPC. The imidazolinic or triazolinic derivative of O-protected ricinoleic acid is used in equimolecular quantities or with moderate excesses with respect to the GPC (II).

The temperature at which the acylation reaction is carried out is between 20 and 80° C. It is preferable to operate at room temperature and the corresponding times are those required to end the reaction.

Step f)

In step (f) of the process of the present invention the protecting group is removed from the hydroxyl group. When the protecting group is MEMCl, the reaction can be carried out according to the method described by Monti et al., 1983 (Synth. Commun., 13, page 1021) which uses the pyridine salt of p-toluenesulfonic acid. This method allows the complete removal of the protecting group, obtaining a deprotected product with a good optical purity.

When the protecting group is TROC, the method described by Windholz and Johnson, (Tetr.Lett. page 2555, 1967) which uses Zn and $CH_3$—COOH, can be used.

The product (I) thus obtained can be further purified adopting one of the conventional techniques.

The homogeneity of the compound thus obtained is tested by gaschromatography, whereas their identity is determined by spectroscopic techniques (NMR, mass spectrometry).

The following examples which have the sole purpose of describing the present invention in more detail, should in no way be considered as limiting the scope of the invention itself.

EXAMPLE 1
Preparation of Ricinoleic Acid (III)

200 g of castor oil, SIGMA) are charged into a 1 litre glass flask equipped with a drip funnel and mechanical stirring, containing a solution of KOH (40 g) in 400 ml of ethanol at 99%. The resulting mixture is heated to 80° C., to reflux temperature, for 15 minutes and then the ethanol is evaporated under vacuum. The solid residue is crushed in 1 litre of ethyl ether until a very fine suspension is obtained. The suspension is filtered and the precipitate is washed twice with 500 ml of diethyl ether and then dissolved in 1 litre of water. It is then acidified to pH 2 with concentrated HCl. The oil which is separated is extracted with petroleum ether. After anhydrification with $Na_2SO_4$ for a night, the mixture is filtered and dried in a Rotavapor under vacuum (25 mm Hg).

150 g of colourless ricinoleic acid are obtained with a titer of 96% (determined by gaschromatography as methyl ester of the acid obtained by treatment with diazomethane). The impurities are: palmitic acid 0.3%, linoleic acid 1.3%, oleic acid 2.0% and stearic acid 0.4%.

EXAMPLE 2
Preparation of Methyl Ester of Ricinoleic Acid (IV)

100 g of ricinoleic acid (III) and 300 ml of methanol are charged into a 1 litre glass flask. Gaseous HCl (30 g) is then bubbled into the solution cooled in a water and ice bath. The solution is maintained, under stirring, at room temperature for 30 minutes. The solution is poured into 500 ml of water and ice and is extracted with petroleum ether. The aqueous phase is separated, the extract is washed twice with water, once with an aqueous solution of $NaHCO_3$ (10%) and is finally anhydrified on $Na_2SO_4$. The solution is filtered and dried under reduced pressure (25 mm Hg).

106 g of methyl ester of ricinoleic acid are obtained. The titer determined by gaschromatography is 96%.

The product is further purified by chromatography on silica gel (80×400 mm) eluating with a mixture of petroleum ether:acetone (90:10 v/v). The impurities are discharged at the head after about 2 l of eluate and the pure product is discharged after about 3 l. After evaporation of the solvent, 98 g of methyl ester of ricinoleic acid, 100% pure, according to gaschromatographic analysis, are obtained.

EXAMPLE 3
A) Protection of the Hydroxyl of Methyl Ester of Ricinoleic Acid with (MEMCl)

38 g of methyl ester of ricinoleic acid (III) are charged into a glass flask containing 200 ml of dichloroethane and 25 ml of N,N'diisopropyl-N-ethylamine.

20 g of MEMCl are then added, dropwise in 2 hours, to the solution cooled to 0° C. The solution is maintained, under stirring, at room temperature for a night. The reaction mixture is poured into 500 ml of an aqueous solution of HCl 2 N and is extracted with dichloroethane. The extract is then washed with water and then with an aqueous solution of $NaHCO_3$ (10%), is anhydrified on $Na_2SO_4$ and dried. Compound (V) is obtained in oily form.

B) Preparation of Compound (VI) by Alkaline Hydrolysis

Compound (V) obtained as described in A) is dissolved in 200 ml of methanol containing 20 g of NaOH and is stirred at room temperature until complete hydrolysis of the ester of ricinoleic acid (V) (a sample diluted with water should give a limpid solution).

The methanol solution is then diluted in 500 ml of water, acidified with an aqueous solution of HCl at 20% and extracted with petroleum ether.

The extract is washed with water, anhydrified with $Na_2SO_4$ and dried under reduced pressure. 34 g of pure O-MEM ricinoleic acid are obtained (according to TLC and NMR analyses).

EXAMPLE 4
A) Protection of the —OH Group of the Methyl Ester of Ricinoleic Acid with Trichloroethylchloroformiate (TROC)

18 g of trichloroethylchloroformiate (TROC) are added dropwise in 2 hours into a glass flask containing 150 ml of diethyl ether, 10 ml of pyridine and 23 g of methyl ester of ricinoleic acid cooled to 5° C.

The solution is maintained, under stirring, at room temperature for a night. The reaction mixture is diluted with 100 ml of petroleum ether, the pyridine hydrochloride is filtered and the solution is dried first under reduced pressure and then under forced vacuum (0.1 mm Hg) at 50° C., to remove the traces of pyridine. 37.8 g of oily product are obtained (V).

B) Enzymatic Hydrolysis 25 g of the product (V) are dispersed, under vigorous stirring, in 300 ml of phosphate buffer 10 mM, pH 7.3. 4 g of lipase from Pseudomonas (Amano PS) are then added to the suspension in an automatic titrator (pHstat). The hydrolysis reaction of the methyl ether is carried out at 35° C. for 24 hours, maintaining the pH constant by the addition of NaOH 0.5 M.

After acidification of the reaction mixture with HCl 2 N, it is extracted with diethyl ether, anhydrified with $Na_2SO_4$ and evaporated under vacuum. 21.4 g of 0-TROC ricinoleic acid are obtained. The product which contains 3–4% of methyl ester can be used as such in the subsequent synthesis step.

It can otherwise be further purified by chromatography on silica gel using a mixture of petroleum:acetone (volumetric ratio 85:15), as eluant.

EXAMPLE 5
Acylation of L-α-glycerophosphatidylcholine (GPC) with Imidazolyl Ricinoleyl O-MEM 8 g of O-MEM ricinoleic acid are dissolved, in a 100 ml flask under a nitrogen atmosphere and under stirring, in 20 ml of anhydrous tetrahydrofuran (THF). 3.4 g of carbonyl-diimidazole are then slowly added and the temperature is left to rise to 40° C. At the end of the development of $CO_2$, the THF is evaporated under vacuum. The residue (11 g) is used as such in the subsequent acylation step.

2.6 g of GPC, 4 g of anhydrous $K_2CO_3$ and 11 g of imidazolyl derivative are added in a 100 ml flask containing 20 ml of dimethylformamide (DMF).

The mixture is stirred for 24 hours at room temperature (25–30° C.) and then diluted with 100 ml of ethyl ether.

After filtration, it is then dried under reduced pressure and then under forced vacuum (0.1 mm Hg) at 40° C. The residue is dissolved in chloroform and subsequently purified on a silica gel column eluating with an initial mixture consisting of chloroform:methanol:water (65:25:2) and then gradually increasing the quantity of water from 2 to 4. After evaporating the fractions containing the pure product, 6.5 g of waxy product are obtained with a structure and physico-chemical characteristics identical to those of the compound having formula (VII).

EXAMPLE 6
Acylation of L-α-glycerophosphatidylcholine (GPC) with O-TROC Ricinoleic Acid 1.8 g (0.007 moles) of GPC and 13.5 g (0.028 moles) of O-TROC ricinoleic acid are charged into a 100 ml flask in a nitrogen atmosphere and under stirring. 15 ml of methanol are then added and the mixture is stirred until complete dissolution. The methanol is subsequently evaporated under vacuum (0.1 mm Hg) heating to 65° C. for 8 hours until a dense suspension is obtained. This is diluted with 30 ml of chloroform and a solution of 4.15 g (0.028 moles) of 4-pyrrolidylpyridine and 5.8 g (0.028 moles) of dicyclohexylcarbodiimide (DCC) in 20 ml of chloroform are added dropwise for 30 minutes. The resulting mixture is maintained, under stirring, at 45° C. for a night.

The mixture is then diluted with ethyl ether (50 ml) and the precipitate is separated by filtration. The solution is dried, the residue dissolved in 50 ml of a mixture of chloroform:methanol (1:1) and charged onto a column (30× 30 cm) of Amberlist® 15 resin (Rohm and Haas) which retains the pyrrolidylpyridine, and eluated with a mixture of chloroform:methanol (1:1, v/v).

The eluate (300 ml) is dried, dissolved in 20 ml of chloroform and then charged onto a silica gel column. Elution is then carried out with a mixture consisting of chloroform:methanol:water with an initial volumetric ratio of 65:25:2, and the quantity of water is then gradually increased from 2 to 4. The fractions containing the desired product are joined and dried under reduced pressure and then under forced vacuum. 3.2 g of white waxy product (VII) are obtained, $[\alpha]^D_{23}=+20.9$.

EXAMPLE 7
Deprotection of the GPC derivative containing the O-MEM group 2 g of product VII and 3 g of pyridine salt of p-toluenesulfonic acid are dissolved in 45 ml of ethylmethylketone. The mixture is heated to 80° C., under reflux nitrogen for 42 hours. The mixture is diluted with ethyl ether, the precitipate is filtered, the solution is dried and the residue redissolved in chloroform. The solution is charged onto a silica gel column. The products are eluted first with chloroform, then with a mixture of chloroform:methanol (65:25, v/v) and then adding water up to 4%.

The fractions containing the pure product are dried, the residue is dissolved in diethyl ether and the solution is treated with an aqueous solution of $NaHCO_3$ at 10%. The ether solution is separated, anhydrified and dried under vacuum. 0.95 g of solid waxy product are obtained, whose structure and physico-chemical characteristics correspond to compound (I), $[\alpha]^D_{23}=+6.1$.

EXAMPLE 8
Deprotection of the GPC derivative containing the O-TROC group 1.5 g of zinc in powder form are dissolved in small amounts in 10 minutes in a mixture of 1.5 ml of water and 15 ml of acetic acid, the temperature being maintained at 15–20° C. The reaction mixture is poured into water (100 ml) and $NaHCO_3$ is added until the solution is neutral. The mixture is extracted with diethyl ether and the extract is then dried. A solid waxy product is obtained, which is purified as described in example 7. After evaporation of the fractions containing the pure product, 0.88 g of solid waxy product are obtained, whose structure and physico-chemical characteristics correspond to compound (I), $[\alpha]^D_{23}=+7.3$.

What is claimed is:

1. A process for the synthesis of diricinoleylphosphatidylcholine in optically active form, which comprises:
    a) esterifying the terminal carboxylic group of ricinoleic acid with an alcohol having from 1 to 4 carbon atoms to give the corresponding ester;
    b) protecting the hydroxylic group of the ester of ricinoleic acid with a protecting group selected from the group consisting of 2-methoxy-ethoxymethylchloride, trichloroethylchloroformiate, chloromethylmethylether and chloromethylmethylsulfide and isolating the ester of ricinoleic acid of which the hydroxylic group is protected;
    c) hydrolyzing the ester of ricinoleic acid of which the hydroxylic group is protected and isolating the ricinoleic acid of which the hydroxylic group is protected;
    d) reacting the hydrolyzed ester of ricinoleic acid of which the hydroxylic group is protected with a compound containing an imidazole or triazole group to produce an imidazolic or triazolic derivative;
    e) acylating L-α-glycerophosphatidylcholine with an imidazolic or triazolic derivative of the compound produced in step d) in an organic solvent, in the presence of an anhydrous alkaline carbonate, and isolating the diricinoleylphosphatidylcholine of which the hydroxylic group is protected;
    f) removing the protecting group from the hydroxylic group of the compound produced in step e); and finally
    g) recovering and purifying diricinoleylphosphatidylcholine by means of chromatography.

2. The process according to claim 1, wherein in step a) the ricinoleic acid is prepared with a purity of more than 99% by extraction of the saponification solution of castor oil with an organic solvent selected from the group consisting of tetrahydrofuran, dioxane, dimethoxyethane and ethers selected from the group consisting of diethyl ether, diisopropyl ether and dibutylether.

3. The process according to claim 2, wherein the solvent is diethyl ether or tetrahydrofuran.

4. The process according to claim 1, wherein in step a) the alcohol is methyl alcohol.

5. The process according to claim 1, wherein in step a) the esterification reaction is carried out by putting ricinoleic acid in contact with the alcohol in a molar ratio between each other of 1:10 to 1:50, in the presence of gaseous hydrochloric acid, at a temperature ranging from 0 to 50° C.

6. The process according to claim 1, wherein the protecting group is selected from the group consisting of 2-methoxy-ethoxymethylchloride and trichloroethylchloroformiate.

7. The process according to claim 1, wherein in step c) the hydrolysis of the ester of ricinoleic acid is carried out in an alkaline environment when the protecting group is 2-methoxy-ethoxymethylchloride.

8. The process according to claim 1, wherein in step c) the hydrolysis of the ester of ricinoleic acid is carried out in the presence of an enzyme lipase when the protecting group is trichloroethylchloroformiate.

9. The process according to claim 8, wherein the solvent is N,N'-dimethylformamide.

10. The process according to claim 1, wherein in step d) the imidazolinic or triazolinic derivative of O-protected ricinoleic acid is used in equimolecular quantities or with moderate excesses with respect to the L-α-glycerophosphatidylcholine.

11. The process according to claim 1, wherein in step d) the acylation reaction is carried out at a temperature ranging from 20 to 80° C.

* * * * *